United States Patent [19]

Bagga et al.

[11] Patent Number: 5,990,384
[45] Date of Patent: Nov. 23, 1999

[54] CO-EXPRESSION OF PROTEINS

[75] Inventors: Suman Bagga; Champa Sengupta-Gopalan; John D. Kemp, all of Las Cruces, N.Mex.

[73] Assignee: New Mexico State University, Las Cruces, N.Mex.

[21] Appl. No.: 08/866,879

[22] Filed: May 30, 1997

Related U.S. Application Data

[60] Provisional application No. 60/020,424, May 31, 1996.

[51] Int. Cl.$^6$ .............................. C12N 5/04; C12N 15/29; A01H 5/00; A01H 5/10
[52] U.S. Cl. ........................ 800/278; 536/23.6; 435/69.1; 435/320.1; 435/410; 435/419; 800/284; 800/295; 800/320.1
[58] Field of Search ......................... 536/23.6; 435/69.1, 435/320.1, 410, 419; 800/200, 205, DIG. 43, DIG. 56, 278, 284, 295, 320.1

[56] References Cited

PUBLICATIONS

Matzke and Matzke. Plant Physiol. 1995. vol. 107: 679–685.
Finnegan and MCElory. Bio/Technology. 1994. 12: 883–888.
Ohtani et al. Plant Molecular Biology. 1990. vol. 16: 117–128.
Giannazza et al. Phytochemistry. 1977. vol. 16: 315–317.
Bagga et al. Plant Physiol. 1995. vol. 107: 13–23. January issue.
Bray et al. Planta. 1987. vol. 172: 364–370.
Kirhara et al. Molecular and general Genetics. 1988. vol. 211: 477–484.
Marks and Larkins. Journal of Biological Chemistry. 1982. vol. 257:9976–9983).
Abe, S. et al. (1991) "Protein bodies in corn endosperm are enclosed by and enmeshed in F.–actin." Protoplasma 165: 139–149.
Maliga, P. (1978) "Resistant mutant and their use in genetic manipulation." Frontiers of Plant Tissue Culture (Ed: Thorpe TA) pp. 381–392.
Argo, P., et al. (1982) "A Structural Model for Maize Zein Proteins" The Journal of Biological Chemistry, vol. 257, No. 17, 9984–9990.
Altenbach, S.B., et al. (1992) "Accumulation of a Brazil nut albumin in seeds of transgenic canola results in enhanced levels of seed protein methionine" Plant Molecular Biology 18: 235–245.
Barnes, D.K., et al. (1988) "Highlights in the USA and Canada" Agronomy Monograph No. 29: 1–24.
Boston, R.S., et al. (1991) "Increased Expression of the Maize Immunoglobulin Binding Protein Homolog b–70 in Three Zein Regulatory Mutants" The Plant Cell, vol. 3, 497–505.
De Clercq, A., et al. (1990) "Expression and Processing of an Arabidopsis 2S Albumin in Transgenic Tobacco" Plant Physiol. 92: 899–907.
Esen, A., et al. (1992) "Immunocytochemical Localization of δ–Zein In The Protein Bodies of Maize Endosperm Cells" American Journal of Botany 79(3): 243–248.

Gianazza, E., et al. (1977) "Amino Acid Composition of Zein Molecular Components" Physiochemistry, vol. 16, 315–317.
Guerche, P., et al. (1990) "Expression of the 2S albumin from *Bertholletia excelsa* in *Brassica napus*" Mol Gen Genet 221: 306–314.
Hoffman, L.M., et al. (1988) "A modified storage protein is synthesized, processed, and degraded in the seeds of transgenic plants" Plant Molecular Biology 11:717–729.
Kaldy, M.S., et al. (1979) "Amino acid composition of sainfoin forage" Grass and Forage Science, vol. 34, 145–148.
Karchi, H., et al. (1993) "Seed–specific expression of a bacterial desensitized aspartate kinase increases the production of seed threonine and methionine in transgenic tobacco" The Plant Journal, 3(5): 721–727.
Kirihara, J.A., et al. (1988) "Differential expression of a gene for a methionine–rich storage protein in maize" Mol Gen Genet 211: 477–484.
Langridge, P., et al. (1983) "A Zein Gene of Maize is Transcribed from Two Widely Separated Promoter Regions" Cell, vol. 34, 1015–1022.
Larkins, B.A., et al. (1989) "Zein Gene Expression during Maize Endosperm Development" The Molecular Basis of Plant Development, pp. 109–120.
Larkins, B.A., et al. (1978) "Synthesis and Deposition of Zein in Protein Bodies of Maize Endosperm" Plant Physiol. 62: 256–263.
Lee, K.H., et al. (1976) "Genetic Regulation of Storage Protein Content in Maize Endosperm" Biochemical Genetics, vol. 14: 641–650.
Lending, C.R., et al. (1989) "Changes in the Zein Composition of Protein Bodies during Maize Endosperm Development" The Plant Cell, vol. 1: 1011–1023.

(List continued on next page.)

*Primary Examiner*—Lynette R. F. Smith
*Assistant Examiner*—Ousama Zaghmout
*Attorney, Agent, or Firm*—Saliwanchik, Lloyd & Saliwanchik

[57] ABSTRACT

The subject invention pertains to materials and methods for transformed plants and plant tissues that are capable of expressing high levels of stable proteins which are localized as protein bodies within the plant cell. Transformed plants co-expressing high levels of both the 15 kD and 10 kD zein proteins are disclosed which accumulate to high levels as protein bodies in the vegetative tissue of the plant. Transformed plants co-expressing the 15 kD and 10 kD zein proteins are useful for providing forage crops containing increased levels of sulfur containing amino acids, such as methionine, in the diet of animals that normally feed on such crops. Also contemplated by the subject invention are transformed plants or plant tissue comprising stable protein bodies which contain heterologous proteinaceous material. In one embodiment, a stable protein body is expressed in a plant or plant tissue as a fusion protein comprising a zein protein and an operably linked protein or peptide. The protein bodies provided in the present invention are resistant to rumin digestion or environmental degradation.

6 Claims, 9 Drawing Sheets

OTHER PUBLICATIONS

Li, X., et al. (1993) "Rice Prolamine Protein Body Biogenesis A BiP–Mediated Process" Science, vol. 262, pp. 1054–1056.

Michaud, R., et al. (1988) "World Distribution and Historical Development", Alfalfa and Alfalfa Improvement—Agronomy Monograph No. 29: 25–91.

Misra, P.S., et al. (1972) "Endosperm Protein Systhesis in Maize Mutants with Increased Lysine Content" Science, vol. 176: 1425–1427.

Ohtani, T., et al. (1991) "Normal and lysine–containing zeins are unstable in transgenic tobacco seeds", Plant Molecular Biology 16: 117–128.

Pelham, H.R.B. (1990) "The retention signal for soluble proteins of the endoplasmic reticulum", Elsevier Science Publishers 0376–5067/90 pp. 483–486.

Phillips, R.L., et al. (1985) "Elevated Protein–Bound Methionine in Seeds of a Maize Line Resistant to Lysine Plus Threonine", American Association of Cereal Chemists, vol. 62, No. 3: 213–218.

Reish, B. et al. (1981) "Selection and Characterization of Ethionine–resistant Alfalfa (*Medicago sativa* L.) Cell Lines" Theor. Appl. Genet, 59: 89–94.

Saalbach, I., et al. (1994) "A chimeric gene encoding the methionine–rich 2S albumin of the Brazil nut (*Bertholletia excelsa* H.B.K.) Is stably expressed and inherited in transgenic grain legumes" Mol. Gen. Genet 242: 226–236.

Schroeder, H.E., et al. (1991) "Expression of a Chicken Ovalbumin Gene in Three Lucerne Cultivars" Aust. J. Plant Physiol. 18: 495–505.

Wallace, J.C., et al. (1988) "Aggregation of Lysine–Containing Zeins into Protein Bodies in Xenopus Oocytes" Science, vol. 240: 662–664.

Williamson, J.D., et al. (1988) "The Synthesis of a 19 Kilodalton Zein Protein in Transgenic Petunia Plants" Plant Physiol. 88: 1002–1007.

Zhang, F., et al. (1992) "Increases in binding protein (BiP) accompany changes in protein body morphology in three high–lysine mutants of maize" Protoplasma 171: 142–152.

CO-EXPRESSION OF PROTEINS

CROSS-REFERENCE TO A RELATED APPLICATION

This application claims the benefit of the filing date of U.S. provisional application Ser. No. 60/020,424 filed as a provisional application under 35 USC 111(b) on May 31, 1996.

BACKGROUND OF THE INVENTION

Alfalfa (*Medicago sativa* L.) is considered to be the most important cultivated forage crop in the world (Hanson et al., 1988; Michaud et al., 1988) and is often referred to as "Queen of the forage crops" because it is widely grown, has a superb balance of vitamins and minerals, is high yielding, is an excellent source of biological nitrogen fixation, and it serves as an attractive nectar source for honeybees (Barnes et al., 1988; Smoliak and Bjorge, 1983). Alfalfa has been bred for years for both forage quality and plant performance. Although alfalfa and other leguminous forage crops are high in protein, these plants are deficient in the sulfur amino acids (S-amino acids), methionine and cysteine (Kaldy et al., 1979). It has been shown that wool growth in sheep is limited by the availability of S-amino acids. Similarly, milk production by dairy animals is affected by the deficiency of S-amino acids in plants. Efforts to use conventional plant breeding and cell selection techniques to increase the S-amino acid content of alfalfa have met with little or no success.

A genetic engineering approach to improve the amino acid balance of alfalfa and other forage crops would be to introduce into these plants genes encoding proteins high in methionine driven by a strong constitutive promoter or a leaf promoter. In order to significantly alter the amino acid balance of legume forage, the foreign proteins should contain about 15 to 25% of S-amino acids and constitute 5 to 10% of the total leaf protein. To achieve these levels of protein accumulation, one has to ensure not only maximum levels of transcription and translation of the gene but also the stability of the protein. In regard to forage crops for ruminant animals, the digestibility of S-amino acid containing proteins by the rumen bacteria and the stomach enzymes is also an extremely critical issue in regard to providing a suitable forage crop for ruminant animals, but is often overlooked. Thus, the S-amino acid rich protein should be relatively resistant to degradation in the rumen (first stomach) of the ruminant animals and should be assimilated in the lower gastrointestinal tract.

Most of the concerted efforts in regard to nutritional improvement in plants has focused on seed proteins. Since corn and other cereal crops are not easily transformable, most work directed to seed protein modification has involved testing stability of modified prolamine proteins in transgenic tobacco (Williamson et al., 1988; Ohtani et al., 1990) and *Xenopus oocytes* (Wallace et al. 1988). The synthesis of lysine containing α zeins was also analyzed in transgenic tobacco and petunia seeds (Williamson et al., 1988; Ohtani et al., 1990). Both the normal and modified protein were found to have a very short half-life.

Efforts to improve the S-amino acid content of legume seed proteins have included introducing a 45 bp oligonucleotide containing six methionine codons into the third exon of a β-phaseolin gene. Transformants containing this modified gene showed that the high methionine phaseolin was synthesized at the same level as the normal protein, but was very unstable and was rapidly turned over (Hoffman et al., 1988). Introduction of the extra amino acids in the β-phaseolin protein probably caused a distortion in its secondary structure making it more susceptible to proteolytic degradation. DeClercq et al. (1990), replaced a 23 amino acid coding segment between the sixth and seventh cysteine residues of Arabidopsis 2S albumin, with three different high methionine coding fragments. These modified Arabidopsis 2S genes were transformed into *A. thaliana, B. napus* and tobacco. There was some accumulation of the protein in the seeds but not as much as predicted. (Chrispeefs, M., personal communication). The gene of the 2S albumin of Brazil nut, which contains up to 19% methionine, and driven by the β-phaseolin gene promoter, has been introduced into tobacco (Guerche et al., 1990), rape (Altenbach et al., 1992) and soybean (Pioneer Seed Co.). Recently, Saalbach et al. (1994) synthesized the 2S albumin gene and engineered it behind the CaMV 35S promoter. The gene, when introduced into tobacco and some grain legumes, showed the highest level of expression in the plant leaves and the protein was localized in vacuoles. However, the Brazil nut albumin protein is extremely allergenic and may not be acceptable for consumption.

One approach to increase the pools of particular amino acids in plants has been to introduce bacterial genes encoding for key regulatory enzymes in amino acid biosynthetic pathways in plants. A bacterial gene encoding for aspartate kinase which is desensitized to feedback inhibition by lysine and threonine was fused to the β-phaseolin gene promoter and introduced into tobacco. The seeds of the transgenic tobacco showed increased levels of free threonine and methionine (Karchi et al., 1993; Galili, 1995).

Very little effort has been made with regards to improving forage crop protein quality. Schoeder et al., (1991) introduced the chicken ovalbumin gene (cDNA), driven by a CaMV 35S promoter, into alfalfa. The transgenic alfalfa plants, however, showed very low level accumulation of the protein in the leaves (0.005%). The basis for such a low abundance of this protein in the transgenic alfalfa leaves was not determined.

Some efforts to obtain alfalfa mutants that have larger free methionine levels have also been attempted at the University of Wisconsin. Cell lines with resistance to growth inhibition by an amino acid analogs reportedly produce higher than normal amounts of the corresponding natural amino acid. Hence, growth on specific amino acid analogs has been used as selection tool to select for plants accumulating high levels of a particular amino acid. Amino acid over-production is usually due to relaxed feedback control of an enzyme involved in its production (Malega, 1978). In an attempt to improve the methionine content of alfalfa, mutagenized suspension culture cells of alfalfa were selected for resistance to growth inhibition by a methionine analog (Reish et al., 1981). A few cell lines containing high methionine pools were obtained, however, regeneration of these cell lines did not produce plants with high methionine content (personal communication, Bingham, ET).

Zeins are a group of alcohol soluble proteins that are synthesized during endosperm development in corn and constitute 50% of the total protein in mature seeds (Lee et al., 1976). The zeins can be divided into four groups, the α, β, γ and δ, based on their solubility (Larkins et al., 1989). The zeins can also be separated by size into groups. The α zeins, which is the most abundant class, are made up of the 22 kD and 19 kD zeins; the central region of these proteins consists of repetitive peptides of about 20 amino acid residues (Argos, 1982). The β zeins comprise the 15 kD zein which contains less proline and glutamine than the α zeins. The γ zeins include the 27 kD and 16 kD class and are very rich in proline (25%). The δ zeins are a relatively minor class consisting of the 10 kD zein (Kirihara et al., 1988). All the zein classes are structurally unique. The repeat regions in the α and γ zeins probably have a major role in the packing of protein bodies. Zeins, in general, contain extremely low levels of the essential amino acids lysine, tryptophan and to a lesser extent methionine. The 15 kD and 10 kD zeins, however, are distinguished by their extremely high methionine content (10% and 22.5%, respectively) (Giannaza et al., 1977).

The zeins are synthesized on the rough endoplasmic reticulum (RER) and they aggregate into protein bodies directly in the RER (Larkins and Hurkman, 1978). Based on the analysis of the zein composition of developing protein bodies in corn endosperm, Lending and Larkins (1989), have proposed a descriptive model for the pattern of zein deposition during protein body formation in corn endosperm: The β and γ zeins are the first to start accumulating within the RER. Subsequently, α zeins begin to accumulate as locules within the β and γ zeins. With time, the a zein locules fuse and form a central core while the β and γ zeins form a continuous layer around the periphery of the protein body. In a separate study, Esen and Stetter (1992), demonstrated that the δ zein occurs throughout the core region of the protein body.

Mutations in maize affect the expression of the different zein genes. Changes in zein gene expression in turn have direct impact on the amino acid composition of the seeds. Seeds of plants homozygous for the recessive mutation opaque-2, have increased levels of lysine compared to the wild-type seeds (Misra et al., 1972). The increase in lysine is due to the reduced expression of the 22 kD α zeins (Langridge et al., 1983). The inbred line BSSS-53 has 30% higher level of seed methionine compared to other inbred lines. This increase in methionine content is because of a two-fold increase in the level of the 10 kD zein (Phillips and McClure 1985).

Proteins that accumulate in the endoplasmic reticulum are known to have the amino acid sequence Lys(his) Asp Glu Leu (K(H)DEL) near their carboxy terminal end which prevents them from exiting into the Golgi (Pelham, 1990). The zeins and other prolamines, however, lack this sequence. A cognate of the 70-kD heat shock protein, BiP which functions as a molecular chaperone has been shown to be involved in the formation of prolamine protein body formation in rice endosperm (Li et al., 1993b). The involvement of BiP in the formation of zein protein bodies is based on the fact that BiP accumulates to high levels in the ER and on the abnormal protein bodies of some of the zein regulatory mutants of corn (Boston et al., 1991; Zhang & Boston, 1992). Overall, however, the mechanisms of zein targeting and assembly in protein bodies are poorly understood and it is not known whether inter- and intra-molecular interactions play a key role in protein body formation. Abe et al. (1991), have suggested that the cytoskeleton plays a role in the biogenesis of zein protein bodies.

As can be understood from the above, there remains a need in the art for plants and forage crops that contain stable protein bodies that are high in S-amino acid content. The subject invention provides a novel and advantageous means for improving the forage quality of plants.

BRIEF DESCRIPTION OF THE DRAWINGS

FIG. 3A. Diagrammatic representation of pM10Z. The construct consists of the CaMV 35S promoter fused at the BglII site to a 470 bp BglII-XhoI fragment containing the coding region of the 10 kD zein gene. This is followed by the NOS 3' terminator of pMON316 (Rogers et al., 1987).

FIG. 3B. Analysis of different independent transformants for the accumulation of the 10 kD zein. EtOH soluble protein extracted from the leaves (equivalent to 50 μg of PBS soluble protein), was subjected to SDS PAGE, transferred to nitrocellulose and followed by immunoblot analysis using the 10 kD zein antibodies. Lanes labeled 1 through 7 (under transformants), contain samples from the leaves of different transformants while lanes 1 and 2 (under control), are leaf samples from nontransformed tobacco plants.

FIG. 3C. Analysis of different plant organs (transformant 6) for the accumulation of the 10 kD zein. EtOH soluble fractions (equivalent to 50 μg of PBS soluble protein) from the varius plant parts indicated, along with 2 μg of corn seed protein were subjected to SDS PAGE followed by western analysis using the 10 kD zein antibodies. UT and Mat stand for untransformed and mature seeds, respectively. Molecular weight standards were included in the gels and the size of two of the relevant markers is indicated.

FIG. 5A. Regions of two mesophyll cells showing several 10 kD zein protein bodies (indicated by arrowheads) in a 10 kD zein transformant.

FIG. 5B. Higher magnification of 10 kD zein protein bodies (indicated by arrowheads).

FIG. 5C. Structure of a 15 kD zein protein body in the mesophyll cell of a 15 kD zein transformant.

FIG. 5D. Immunolocalization of 10 kD zein in the leaf cells of a 10 kD zein transformant with the 5 nm gold particles (indicated by arrowheads).

FIG. 6A. EtOH soluble fraction from the leaves (equivalent to 10 μg of PBS soluble protein) and seeds (equivalent to 50 μg of PBS soluble protein) of the 10 kD and 10 kD/15 kD zein plants were subjected to SDS PAGE followed by western analysis using the 10 kD zein antibodies.

FIG. 6B. Quantification of band intensity from FIG. 6A using the Bio Image Intelligent Quantifier.

FIG. 6C. EtOH soluble fraction from the leaves and seeds (equivalent to 50 μg of PBS soluble protein) of the 10 kD and 10 kD/15 kD zein plants were subjected to SDS PAGE followed by western analysis using the 15 kD zein antibodies.

FIG. 6D. Quantification of band intensity from FIG. 6C using the Bio Image Intelligent Quantifier.

FIG. 7A. Conventionally fixed and stained sections of leaves from a 10 kD/15 kD zein plant. Arrowheads point to the protein bodies formed in the cytoplasm.

FIG. 7B. Immunolocalization of the 10 kD zein protein using mouse anti-10 kD zein antibody diluted 1:50 followed by 10 nm diameter gold-conjugated goal anti-mouse IgG.

FIG. 7C. Co-immunolocalization of the 10 kD and 15 kD zeins using the mouse anti-10 kD zein antibody and the rabbit anti-15 kD zein antibodies followed by 10 nm diameter gold conjugated goat anti-mouse IgG and 5 nm gold conjugated goat anti rabbit IgG.

FIG. 7D. A higher magnification of a region showing double-labeling from panel C. The arrowheads point to the 10 nm gold particles while the arrows point to the 5 nm gold particles.

Figures 1A, 1B:
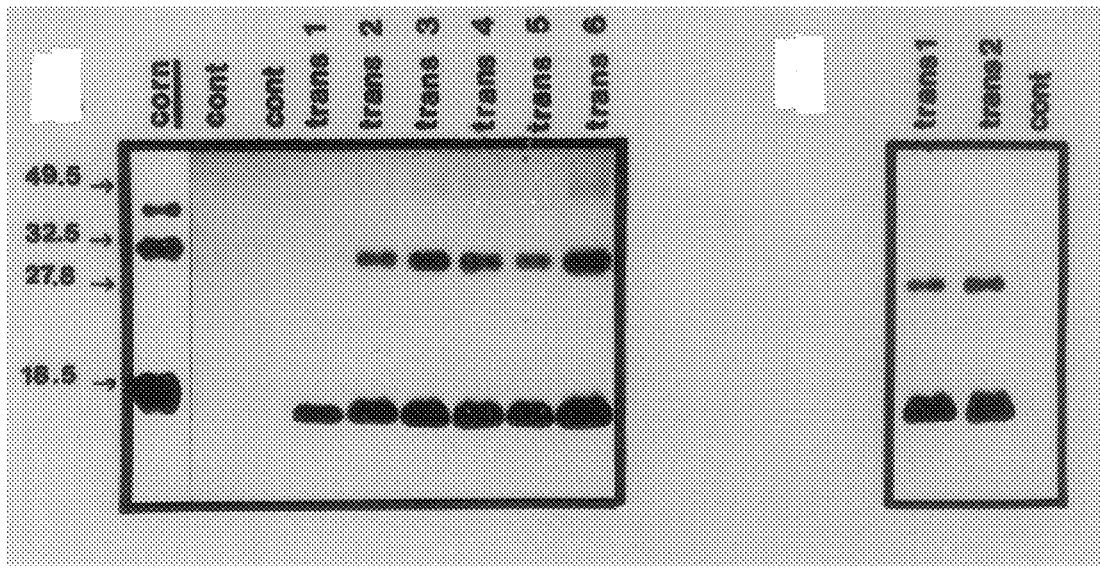
FIGS. 1A–1B show a steady-state accumulation pattern of the 15 kD zein protein in leaves of transgenic *L. japonicus* (panel A) and alfalfa Regen SY (panel B). 70% ethanol soluble protein (equivalent to 50 μg of the phosphate buffered saline soluble fraction) from leaves of different independent transformants was subjected to SDS-PAGE, electroblotted onto nitrocellulose and followed by immunoblot analysis using the 15 kD zein antibody.

Phosphate buffered saline soluble extract (100 μg of protein) from leaves of a control (NT), δ-zein, β-zein and δ-/β-zein plants were subjected to SDS PAGE followed by western blotting using an antibody raised to BiP from maize. A positive control lane containing purified BiP (1 μg) was included in the gel. The lower panel represents the results of band quantification using the Intelligent Quantifier.

BRIEF SUMMARY OF THE INVENTION

The present invention relates to the co-expression of proteins that results in a greater accumulation in a cell of one of the proteins when compared to the levels of the same protein when expressed alone. The proteins are expressed in prokaryotic or eukaryotic cells. One or both of the proteins are accumulated in the cell at higher levels when expressed together than when the proteins are expressed alone in a cell. Standard, routine genetic engineering techniques are employed to (i) isolate the appropriate DNA encoding desired proteins including regulatory sequences, (ii) transform a target cell and, in the case of plants, to regenerate a transgenic plant. The transgenic cells are grown under conditions sufficient to result in the accumulation of one or both proteins at high levels. The proteins accumulated in the cell exhibit increased stability and resistance to degradation.

The subject invention also concerns plants and plant tissues that are capable of expressing high levels of stable proteins which are localized as protein bodies within the plant cell. Specifically exemplified are plants co-expressing both the 15 kD and 10 kD zein proteins. Transformed plants co-expressing the 15 kD and 10 kD zein proteins are useful for providing forage crops containing increased levels of sulfur containing amino acids, such as methionine, in the diet of animals that normally feed on such crops. Also contemplated by the subject invention are plants or plant tissues containing novel heterotypic protein bodies elevated in one or more other essential amino acids (e.g., arginine, histidine, leucine, isoleucine, lysine, phenylalanine, threonine, tryptophan, tyrosine and valine). Also contemplated by the present invention are protein bodies which result in the enhanced accumulation of normally unstable proteins in plant tissue.

The subject invention also concerns plants or plant tissue comprising rumin stable protein bodies which contain other proteinaceous material, for example, an antigenic determinant capable of eliciting an immune response, a proteinaceous drug, pesticide or antimicrobial peptide. Heterologous proteins can be expressed in plants transformed with the storage proteins of the subject invention which can act as a "carrier protein," whereby the proteins coalesce and accumulate in the cell as a protein body. In an alternative embodiment, a rumin stable protein body is provided in a plant or plant tissue as a fusion protein expressed in the cell comprising a zein protein and a heterologous protein or peptide.

DETAILED DESCRIPTION OF THE INVENTION

The subject invention concerns plants and plant tissues that are capable of expressing high levels of stable storage proteins which are localized as protein bodies within the plant cell. Plants contemplated within the scope of the invention include forage crop plants, including, for example, alfalfa, clover, corn silage, sorghum and other leguminous crops, transformed to express the proteins of the invention. Also contemplated within the scope of the present invention are plants for human consumption which have been transformed to express proteins that enhance the protein quality of the plant for improved nutrition. Specifically exemplified are plants expressing proteins containing high levels of S-amino acids, such as methionine and cysteine. In a preferred embodiment, a zein protein is expressed in the plant or plant tissue. More preferably, the zein protein expressed is the 15 kD or 10 kD zein protein. Most preferably, both the 15 kD and 10 kD zein proteins are co-expressed in the plant or plant tissue. Plants having genotypes carrying the 10 kD and 15 kD zein genes were sexually crossed to create hybrids carrying both constructs. The zein proteins expressed in the transformed plants are resistant to rumin degradation and, therefore, are useful for providing nutritionally important amino acids that can be digested in the stomach and absorbed by the ruminant animal because of the protein's capacity to "by-pass" the rumin.

Also contemplated by the subject invention are plants or plant tissue comprising rumin stable protein bodies which contain other proteinaceous material, for example, an antigenic determinant capable of eliciting an immune response, a proteinaceous drug, pesticide or antimicrobial peptide. Heterologous and endogenous proteins and synthetic peptides having essential amino acids can be expressed in plants transformed with the storage proteins of the subject invention which can act as a "carrier protein," whereby the proteins coalesce and accumulate in the cell as a protein body. In an alternative embodiment, a rumin stable protein body is expressed in a plant or plant tissue as a fusion protein comprising a zein protein and a heterologous protein or peptide. The fusion protein can be designed to yield the heterologous protein portion by cleavage with a selected enzyme or under certain physiological conditions. Preferably, the zein protein expressed as part of the fusion protein is the 15 kD or 10 kD zein protein. More preferably, both the 15 kD and 10 kD zein proteins are co-expressed in the plant or plant tissue comprising the fusion protein.

The subject invention also pertains to a rumin stable protein body. Rumin stable protein bodies of the invention are not subject to digestion by rumin bacteria in the rumin of an animal but can be digested proteolytic enzymes of an animal's stomach. A rumin stable protein body of the present invention can be prepared which contains heterologous proteinaceous material in addition to the rumin stable protein. For example, an antigenic determinant capable of eliciting an immune response, a proteinaceous drug, pesticide or antimicrobial peptide. Rumin stable protein bodies can be isolated from plants that have been transformed with polynucleotide molecules encoding the desired rumin stable proteins. Plant cells expressing the polynucleotide molecules encoding the desired rumin stable proteins can be readily selected and regenerated into plants or plant tissue using standard techniques known in the art.

In one embodiment of the present invention, a storage protein gene is co-expressed in a cell with a second protein gene whereby the second protein is accumulated in the cell at a level that is higher than when the second gene is expressed alone in the cell, i.e., in the absence of the storage protein gene. In a preferred embodiment, the storage protein gene is a seed storage protein gene, the target cell is a plant cell and the second protein gene can be any gene encoding a desirable protein. Regulatory sequences employed with the protein genes (promoters, initiation sequences, termination sequences, polyadenylation sequences, enhancers, etc) are readily chosen by one of ordinary skill in the art based on a variety of factors, such as, for example, i) the specific protein genes employed, ii) the target cell to be transformed, iii) the plant tissue where expression/accumulation is desired, iv) the particular plant (monocot, dicot, etc) species to be transformed, etc. For example, when a plant cell is the target cell then a constitutive promoter may be chosen (e.g., CaMV 35S, ubiquitin, etc) or a tissue specific promoter may be employed that will express at high levels in specific tissues (seeds, green tissues, etc).

In another embodiment of the present invention, a 15 kD zein protein gene is employed with a second protein gene in a plant cell that results in accumulation of the second protein in the plant cell. The genes can be contained on a single expression cassette and inserted into the plant genome employing standard transformation and regeneration techniques. Alternatively, the protein genes can be inserted into a plant cell genome independently in separate expression cassettes and transgenic plants can be regenerated therefrom. Also, the protein genes can be inserted into separate plant cells and regenerated into fertile, transgenic plants each containing one of the protein genes. These transgenic plants can then be cross fertilized employing standard plant breeding techniques to result in a cross that contains both the 15 kD zein protein gene and the second protein gene wherein the second protein is accumulated in one or more plant tissues.

In a preferred embodiment of the present invention, alfalfa, tobacco or other plant cells are transformed with a 15 kD zein protein gene and a 10 kD zein protein (second protein) wherein both genes are driven by a constitutive promoter. Fertile, transgenic plants containing both gene constructs are regenerated. Progeny plants are grown and the 10 kD zein protein is accumulated in green tissue at level of 5 to 10 times or more when compared to the accumulation level of the 10 kD protein when expressed alone.

Additionally, the present invention encompasses novel protein bodies formed as a result of expressing a storage protein gene and a second protein gene in green plant tissues. In one embodiment, the novel protein body comprises a 15 kD zein protein and a second protein. The protein body is typically located in leaf tissue. In a preferred embodiment, the novel protein body is located in leaf tissue and comprises a 15 kD zein protein and a 10 kD zein protein.

The subject invention also concerns a method for increasing the forage quality of a plant comprising transforming a plant or plant tissue with a polynucleotide molecule that encodes a storage protein of the present invention. Methods for transforming plants and selecting for expression of the transformed genotype are known in the art. In a preferred embodiment of the method, the polynucleotide encodes a zein protein which is expressed in the plant or plant tissue. More preferably, the zein protein expressed is the 15 kD or 10 kD zein protein. Most preferably, both the 15 kD and 10 kD zein proteins are co-expressed in the transformed plant or plant tissue. Transgenic plants can be readily prepared from the transformed plant or plant tissue using standard techniques known in the art.

The subject invention also concerns methods for increasing the stability and storage of a heterologous protein in a plant or plant tissue. Heterologous proteins can be expressed in plants transformed with the storage proteins of the subject invention which can act as a "carrier protein," whereby the proteins coalesce and accumulate in the cell as a protein body. In an alternative embodiment of the subject method, a plant is transformed with a polynucleotide molecule that encodes a fusion protein comprising a storage protein of the present invention operably linked with a heterologous protein or peptide.

The zein proteins of the present invention include not only those proteins having the same amino acid sequence as found in nature, including allelic variants, but also includes those variant zein proteins having conservative amino acid substitutions, additions and deletions in the protein sequence, as long as the variant protein retains substantially the same relevant biological activity as the native zein protein. The skilled artisan, having the benefit of the teachings disclosed herein, can readily determine whether a variant protein retains the substantially the same biological activity as the non-modified protein.

Materials and Methods

Recombinant DNA Techniques

Standard procedures were used for recombinant DNA manipulations (Maniatis et al., 1982). Plasmid pMZEI10k containing the 10 kD zein cDNA isolated from a corn endosperm cDNA library (Kirihara et al., 1988), was a gift from Dr. J. Messing. A 470 bp EcoR1/Xba1 fragment containing the entire coding region was removed from pUC 119 and cloned into the EcoR1 and Xba1 sites of pSP73. The stop codon for the 10 kD zein is contained within the Xba1 site. The 10 kD zein gene was then recovered as a BglII/XhoI fragment and inserted into the BglII and XhoI sites in the polylinker of pMON316 (Rogers et al., 1987). The translation terminator following the stop codon of the 10kD zein is the NOS terminator. The resulting plasmid was called pM10Z (FIG. 1A). Plasmid pMEZ is as described by Bagga et al. (1995).

Plant Transformation and Regeneration

The plasmid pM10Z was mobilized from *E. coli* DH5α into the *Agrobacterium tumefaciens* receptor strain pTiT37ASE by triparental mating (Rogers et al., 1987). *Nicotiana tabacum* cv Xanthi was transformed by the leaf disc procedure (Horsch et al., 1987). Transformants were selected and regenerated on MS media containing 100 μg of kanamycin/ml shoots appeared within 4–6 weeks after inoculation. The shoots were rooted on the same media without hormones and transferred to the soil.

To obtain the 10 kD zein/15 kD zein plants containing both the zein genes driven by the CaMV35S promoter, tobacco transformants containing either the pM10Z or pMEZ were crossed and the seeds obtained were germinated on media containing 200 μg/ml of kanamycin. Western analysis was performed with protein extracts from the seedlings using both 15 kD zein and 10 kD zein antibodies. Plants expressing both the zein genes (10 kD/15 kD zein plant) and the parent plants (10 kD zein and 15 kD zein plants) were used in all comparative analysis.

Zein Extraction and Western Analysis

Plant tissues were ground and extracted in phosphate buffered saline (PBS) and centrifuged. The supernatant was used for protein determination using the Bradford assay (BIO RAD). The pellet from centrifugation was incubated in 70% ethanol containing 1% of mercaptoethanol at 65° C. for 30 minutes to extract the zein proteins. For western analysis, the EtOH-extractable fraction equivalent of a known amount of PBS soluble protein extract was subjected to SDS-PAGE (Laemmli, 1970), followed by electroblotting onto nitrocellulose membrane. The membrane was blocked for 1 to 2 hrs with 1% BSA in Tris-buffered saline containing 0.05% Tween 20 (TBST), followed by overnight incubation in the same solution containing the appropriate antibodies. The 10 kD zein monoclonal antibodies were provided by DEKALB Genetics Corporation, the 10 kD zein polyclonal antibodies by Dr. J. Messing and the 15 kD zein polyclonal antibodies by Dr. B. Larkins. The protein bands reacting with the antibodies were made visible by using an alkaline phosphatase-linked second antibody (goat antibody or rabbit IgG in case of the polyclonal antibody or mouse IgG in the case of the monoclonal antibody) and the substrates, nitroblue tetrazolium and 5-bromo-4-chloro-3-indolyl-phosphate according to the manufacturer's instructions (Promega). Both the polyclonal and monoclonal antibodies for the 10 kD zein gave similar results on western analysis and immunolocalization on the 10 kD zein plants, but the polyclonal antibodies showed some degree of cross-reactivity with the 15 kD zein and as such in all our comparative analysis involving the parents and the crossed progeny, only the monoclonal antibodies were used.

Analysis of BiP

The phosphate buffered saline (PBS) soluble extracts from the leaves of the different plants were subjected to SDS PAGE followed by western analysis using the polyclonal antibodies for maize BiP (provided by Dr. R. Boston) using the procedure described in zein extraction and western analysis section above.

In vivo labeling of leaf discs

Four leaf discs (7 mm in diameter) from young expanding leaves were incubated in 120 μl of labeling mix (1 mM potassium phosphate, pH 6, 1% sucrose and 50 μg of chloramphenicol) containing 120 μci of 35S methionine (specific activity 1047 ci/mMol), for 2 hours in the light. The discs were then washed well with the incubation buffer and the samples ground in cold PBS. The samples were extracted in PBS, protein estimation made in the PBS soluble fraction and the zeins were recovered from the pellet as described by Bagga et al. (1995). The proteins were analyzed by SDS PAGE followed by electroblotting on PVDF membrane (Millipore). The membrane was sprayed with Enhance (NEN), air dried and exposed to X-ray film.

Electron Microscopy

Small pieces of leaf and seed tissue were fixed in 2.5% glutaraldehyde in 0.07 M sodium cacodylate buffer for 2 h and then postfixed in 1% aqueous osmium tetroxide for 1 hr. The samples were dehydrated in EtOH and embedded in Spurr's resin at 70° C. Silver sections on copper grids were then stained in uranyl acetate and Reynold's lead citrate. The grids were examined in a Hitachi H7000 transmission electron microscope.

Immunoelectron Microscopy

Small pieces of leaf and seed tissue were fixed for 2 h on ice in 4% paraformaldehyde and 0.6% glutaraldehyde in 0.33 M sodium/potassium phosphate buffer (pH 7.3) containing 0.1 M sucrose. The tissue was washed in three changes of buffer containing 7% sucrose and kept in the last change overnight at 4° C. Two different protocols were used at this stage: the fixed tissue was dehydrated in EtOH, infiltrated with Lowicryl at −10° C. and resin was polymerized under UV light at −10° C. for 24 hr and then at room temperature for 24 hr. In the second protocol the tissue was dehydrated in EtOH and embedded in either Spurr's resin or LR White resin and polymerized at 50° C. The remaining steps were all done at room temperature. (The different resins were purchased from Electron Microscopy Sciences, Ft. Washington, Pa.) Silver sections on nickel grids were first incubated in a blocking solution of 10 mM Tris-saline containing 1% BSA (Sigma), 0.05% Tween 20 (Sigma), and 15 mM NaCl. This buffer mixture was used in all of the remaining steps. For immunolabeling seed sections, 5 to 20% normal serum from the animal source of the antibody was added to the blocking solution in order to reduce non-specific staining.

Immunolabeling with the 10 kD zein antibodies: The grids of sections from the 10 kD and 10 kD/15 kD zein crosses were drained and incubated with the monoclonal antibody to 10 kD zein diluted 1:50 in buffer for 45 min to 4 h. Controls were incubated in nonimmune mouse IgG. They were then washed in the buffer and placed in gold-labeled, goat anti-mouse IgG with a diameter of 10 nm (Sigma) diluted 1:50 in buffer for 45 min. In case of the sections from the 10 kD zein plant, the grids were incubated with the polyclonal rabbit anti-10 kD zein diluted 1:1000 in buffer for 60 min. They were then washed and incubated in a solution of gold-conjugated anti-rabbit IgG with a diameter of 5 nm, diluted 1:50 for 60 min. Since the polyclonal 10 kD zein antibody cross-reacted with the 15 kD zein, in case of the 10 kD/15 kD zein cross, the grids were incubated with the 10 kD zein monoclonal antibody followed by gold-conjugated anti-mouse IgG with a diameter of 10 nm. The grids were washed in Tris-Saline containing Tween 20 and 1% BSA, followed by double-distilled water. The grids were then examined either unstained or lightly poststained in uranyl acetate and lead citrate.

Double-labeling with the 10 kD and 15 kD zein antibodies: The grids were incubated in rabbit anti-15 kD zein diluted to 1:100 for 45 to 60 min. The grids were washed and incubated in gold-conjugated goat anti-rabbit IgG with a diameter of 5 nm, diluted 1:50 for 45–60 min. The grids were then thoroughly washed in the buffer and then incubated with mouse anti-10 kD zein diluted 1:50 in buffer for 45 to 60 min. They were then washed in buffer followed by distilled water and incubated in gold-conjugated goal anti-mouse IgG with a diameter of 10 nm diluted 1:50 in buffer for 45 min. The grids were washed in Tris-Saline containing Tween 20 and 1% BSA, followed by double-distilled water. The grids were then examined either unstained or lightly poststained in uranyl acetate and lead citrate.

Following are examples which exemplify certain embodiments of the subject invention. These examples are illustrative and should not be construed as limiting the subject invention in any manner.

Example 1

Figures 2A, 2B:
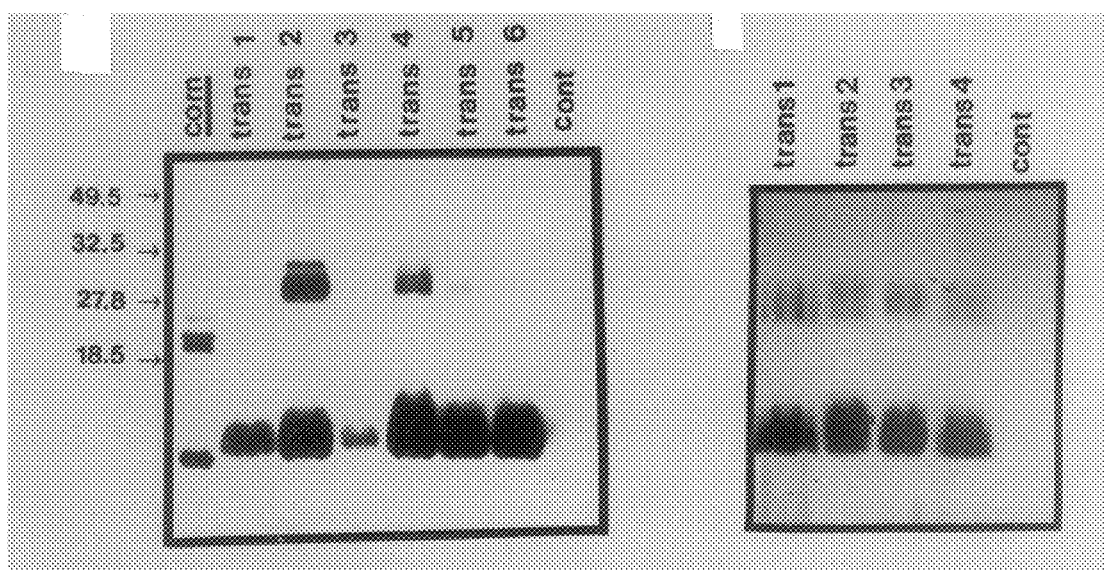
FIGS. 2A–2B show a steady-state accumulation pattern of the 10 kD zein protein in leaves of transgenic *L. japonicus* (panel A) and alfalfa, Regen SY (panel B). 70% ETOH-soluble protein (equivalent to 50 μg of the phosphate buffered saline (soluble fraction) from leaves of different independent transformants was subjected to SDS-PAGE, electroblotted onto nitrocellulose and followed by immunoblot analysis using the 10 kD zein antibody.
Figure 1C:
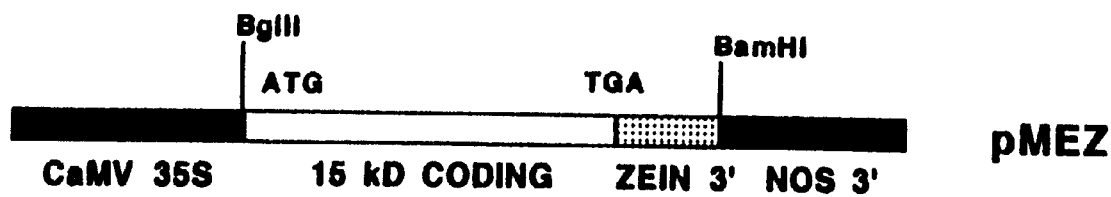
FIG. 1C shows a diagrammatic representation of the 15 kD zein gene construct.
Figure 2C:
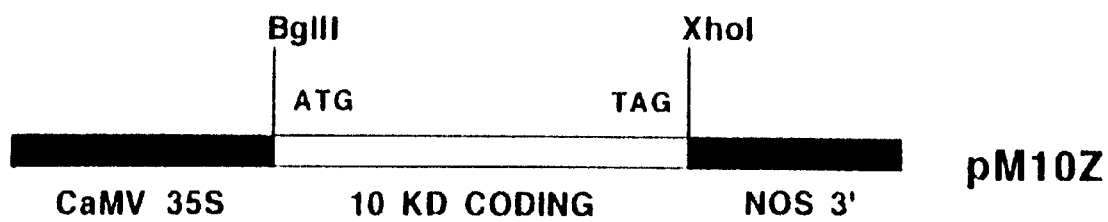
FIG. 2C shows a diagrammatic representation of the 10 kD zein gene construct.

Accumulation of the 15 kD and 10 kD Zeins in Vegetative Tissues of L. japonicus and Alfalfa 15 kD and 10 kD zein coding sequences under the control of a CaMV 35S promoter were introduced into L. japonicus and alfalfa (Regen SY). As shown in FIGS. 1 and 2, both zein proteins showed high levels of accumulation in the vegetative tissues of all the transformants (1 to 2% of total protein). In contrast, the β-phaseolin gene driven by the CaMV 35S promoter, showed constitutive accumulation of the transcripts but, only seed specific accumulation of the protein. The results suggest that the zeins are stable in vegetative tissues while β-phaseolin, which is a vacuolar protein, is not. The stability of the zein proteins can be attributed to the intrinsic properties of the protein or to its subcellular location.

Example 2

Accumulation of Zein Protein in Vegetative Tissues of Tobacco Transformants

Figure 3A:
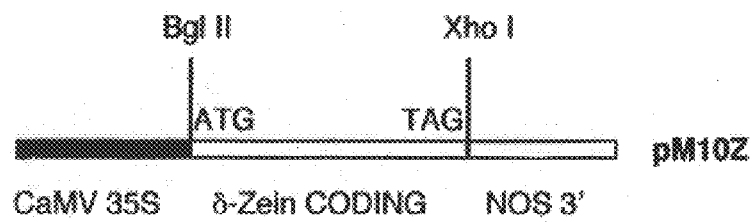
FIGS. 3A–3C show a steady-state accumulation pattern of the 10 kD zein in transgenic tobacco.
Figure 3B:
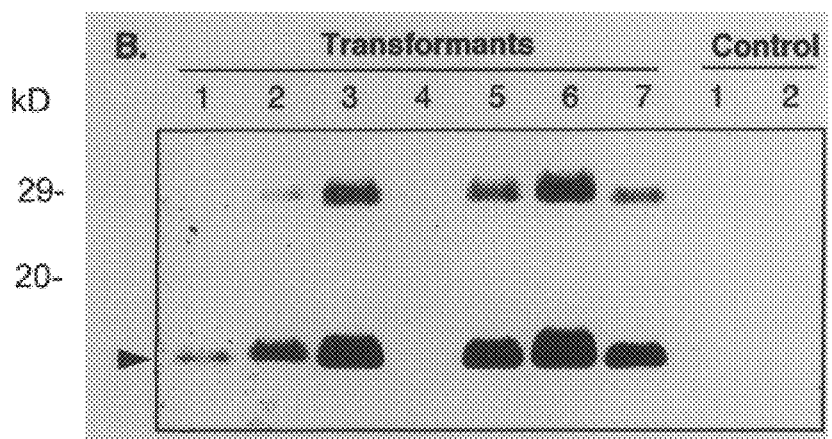
Figure 3C:
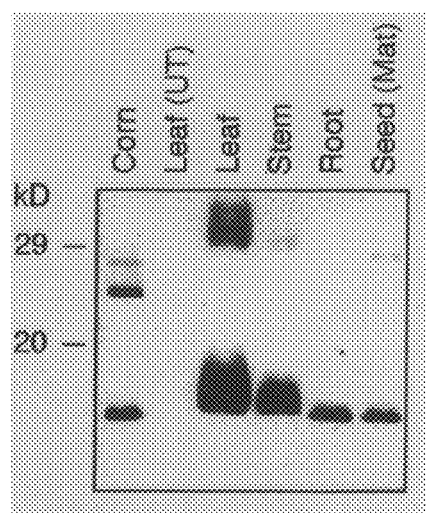

Tobacco plants were transformed with the gene construct pM10Z, consisting of the 10 kD zein gene driven by the CaMV 35S promoter (FIG. 3A). Leaves from seven randomly picked independent transformants were subjected to western analysis to measure the accumulation of 10 kD zein (FIG. 3B). All of the transformants showed two immunoreactive proteins, one of which co-migrated with the 10 kD zein from corn seeds (position indicated by arrow) and the other as a 29 kD band. The latter did not co-migrate with the higher molecular weight immunoreactive band seen in corn seeds (FIG. 3C). The 29 kD immunoreactive band obtained from the leaves of the transgenic plants probably represents an aggregate of the 10 kD zein and another endogenous leaf protein. Similarly, the 20 kD immunoreactive protein band in the corn seed may represent an aggregate of the 10 kD zein with an endogenous corn protein. The accumulation of the 10 kD and the 29 kD immunoreactive bands differed by about 10 fold among the different transformants. Transformant 4 showed almost negligible level of both the immunoreactive bands. Differences in the amount of accumulation of the 10 kD zein in the various transformants can probably be attributed to position effect or the number of copies of the integrated gene.

To determine the accumulation of 10 kD zein protein among different plant parts, equal amounts of protein extract (equivalent of 50 μg of PBS soluble protein) from the leaf, stem, root and seeds of transformant 6 were subjected to western analysis along with corn seed extract (equivalent of 2 μg PBS soluble fraction) (FIG. 3C). The leaves showed the highest level of accumulation of 10 kD zein followed by the stem. The seeds had about a 10-fold lower level of 10 kD zein compared to leaves, as was the case with the 15 kD zein in transgenic tobacco (Bagga et al., 1995). Taken together, our results suggest that 10 kD zein accumulates to significant levels in all organs of transgenic tobacco, as we had reported earlier for 15 kD zein (Bagga et al., 1995).

Example 3

Stability of Zein in Germinating Tobacco Seeds

Figure 4:
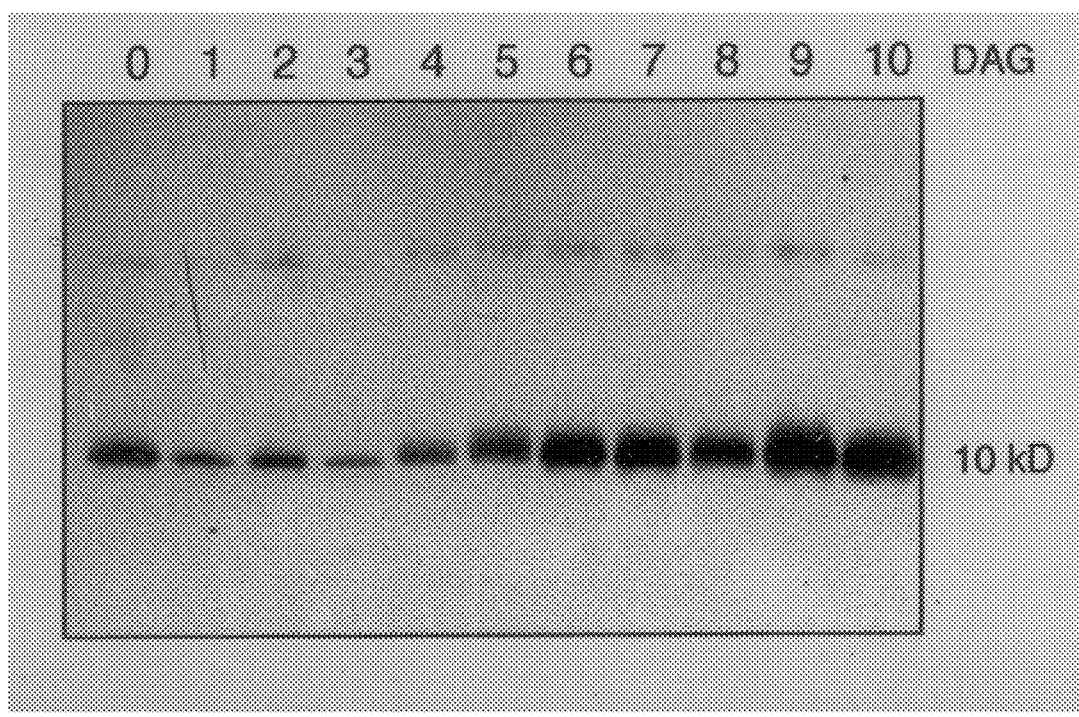
FIG. 4 shows the fate of 10 kD zein in germinating seeds/seedlings of transgenic tobacco. Seeds of a 10 kD zein plant were sterilized and allowed to germinate under sterile conditions and at defined times as indicated in the Figure, seeds/seedlings were harvested and the EtOH soluble fraction extracted. EtOH soluble fraction equivalent of 50 μg of PBS soluble protein was then subjected to SDS PAGE followed by western analysis using the 10 kD zein antibody. The position of the 10 kD zein on the gel is indicated and DAG stands for days after germination.

It was previously shown that the 15 kD zein in transgenic tobacco seeds is not proteolytically digested during germination (Hoffman et al., 1987; Bagga et al., 1997). To determine if the 10 kD zein behaves in a similar manner, seeds from a 10 kD zein plant were allowed to germinate for different time periods (0 to 10 days), the seeds/seedlings harvested and their ethanol-soluble proteins extracted and analyzed by western analysis using the 10 kD zein antibodies (FIG. 4). The level of 10 kD zein remained essentially unchanged for the first four days of germination, after which the level showed a dramatic increase in concentration. A slight drop in the level of the 10 kD zein was observed between 0 and 1 day after germination (DAG), but after that the level was maintained till 4DAG. The drop observed with the 3DAG sample was not consistent within different experiments and is attributed to lower load of the protein extract in that lane. The 4DAG time point coincided with the appearance of the first set of green leaves and may be related to the activation of the CaMV 35S promoter in the developing seedling. The immunoreactive 10 kD zein band also appeared fairly diffused in SDS-gels of proteins from the seedling stage, as has been observe with the leaf sample, suggesting that the leaves have some material in the ethanol-soluble protein fraction that interferes with the mobility of 10 kD zein. These results suggest that 10 kD zein is not degraded during germination of tobacco seeds.

Example 4

Immunolocalization of the 15 kD and 10 kD Zein Proteins in Novel Protein Bodies in Transgenic Plants To understand the basis for the stability of the 15 kD and 10 kD zein proteins in the leaves of transgenic plants, the location of these proteins at a subcellular level was examined. Leaves of the transformants, along with control plants, were subjected to ultrastructural analysis followed by immunocytochemistry (using 15 kD and 10 kD zein antibodies). The 15 kD zein protein appears to be uniformly distributed in unique rosette-shaped protein bodies lined by RER. (Bagga et al., 1995, Appendix). These protein bodies were also seen in *L. japonicus* and alfalfa expressing this 15 kD zein gene.

Figures 5A, 5B:
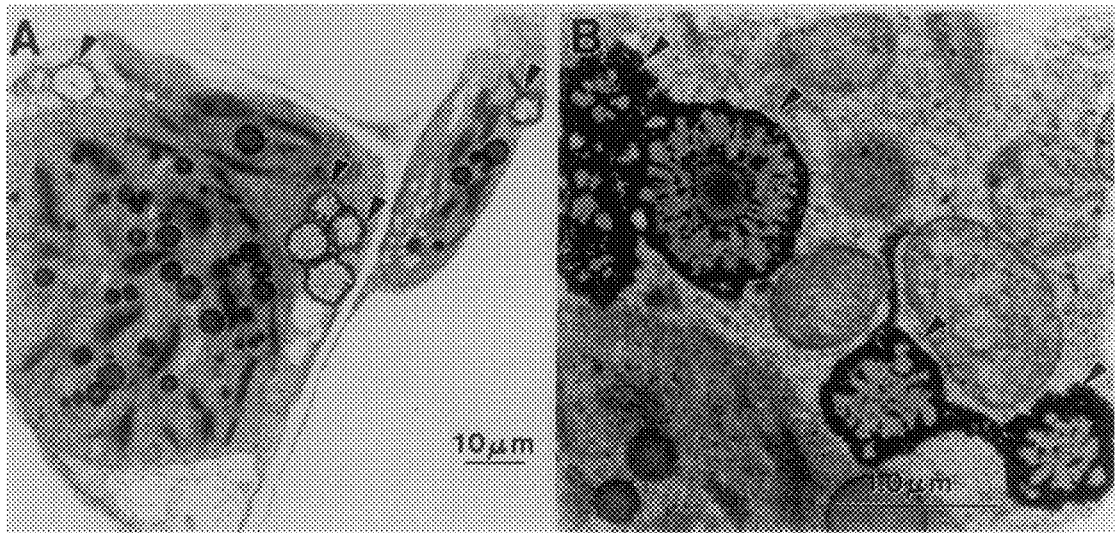
FIGS. 5A–5D. Ultrastructure and Immunogold localization of 10 kD zein in transgenic tobacco leaves.
Figures 5C, 5D:
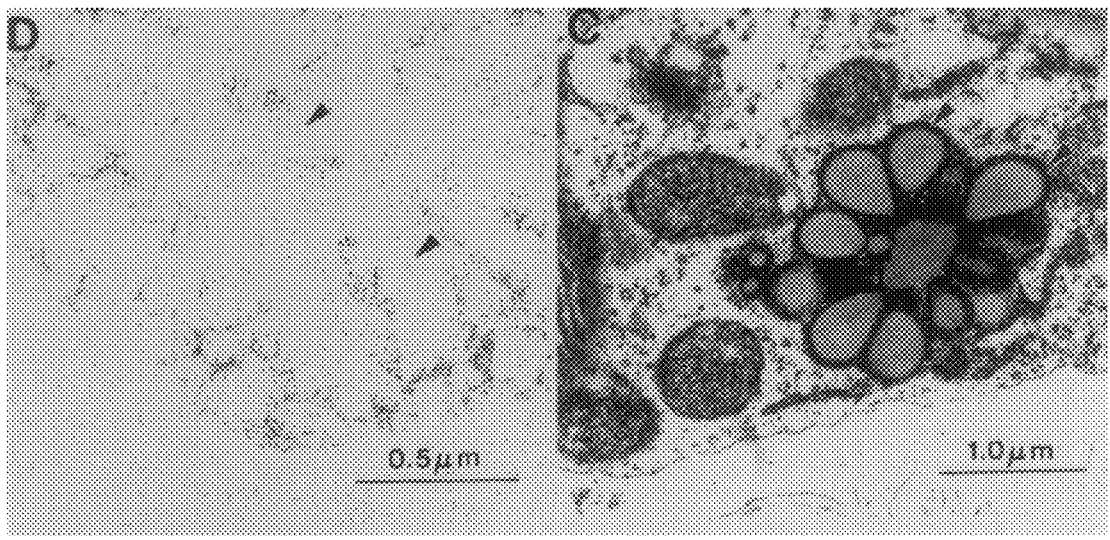
Figure 6A:
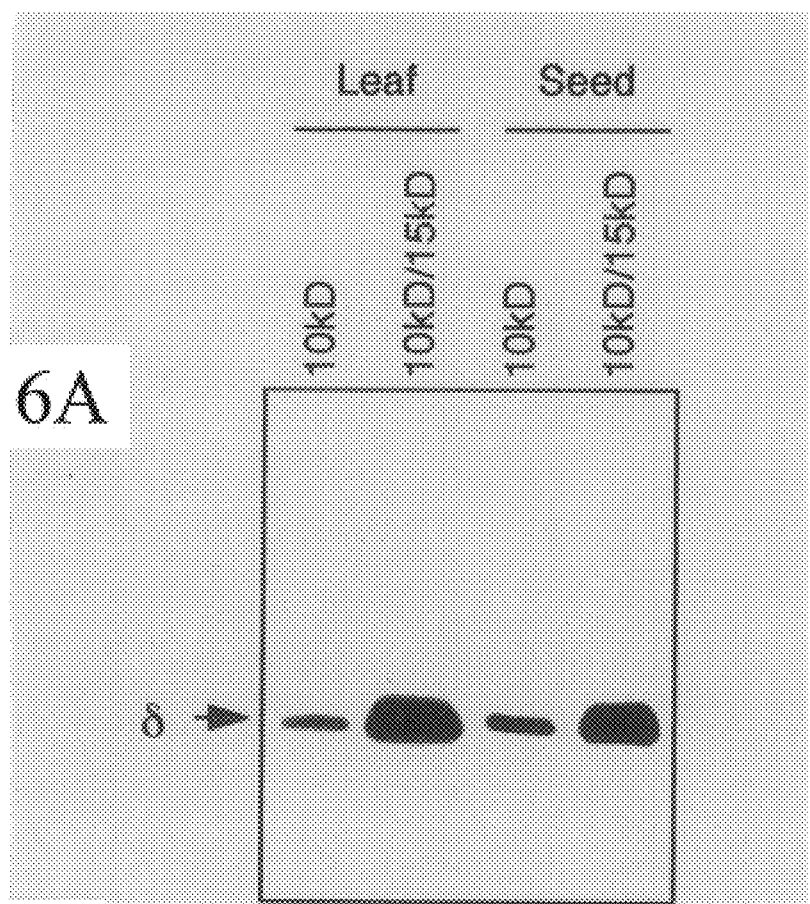
FIGS. 6A–6D. Comparison of 10 kD and 15 kD zein levels in the leaves and seeds of the 10 kD, 15 kD and 10 kD/15 kD zein plants.
Figure 6B:
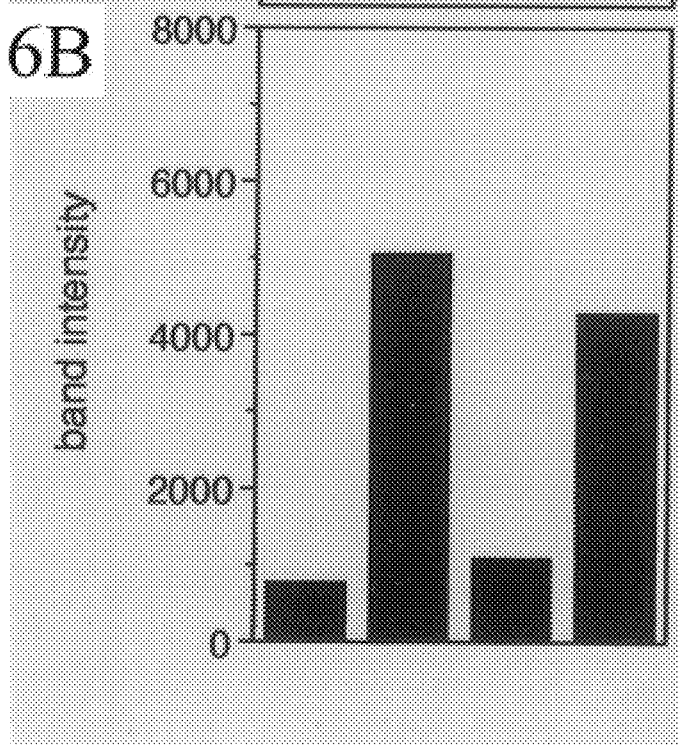
Figure 6C:
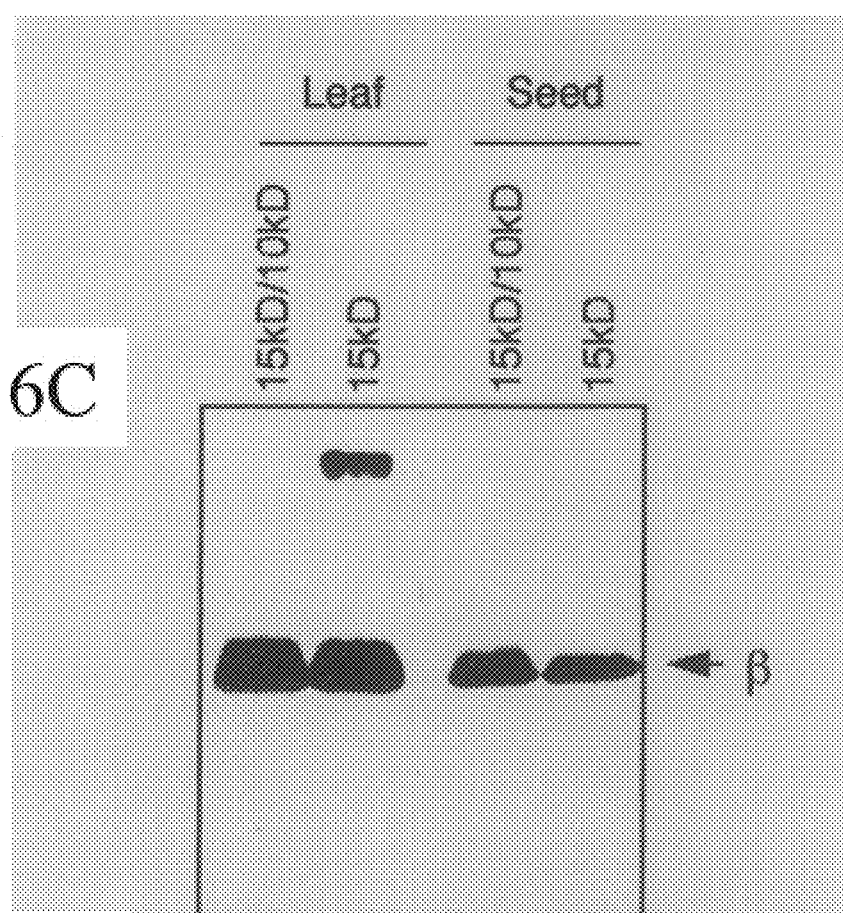
Figure 6D:
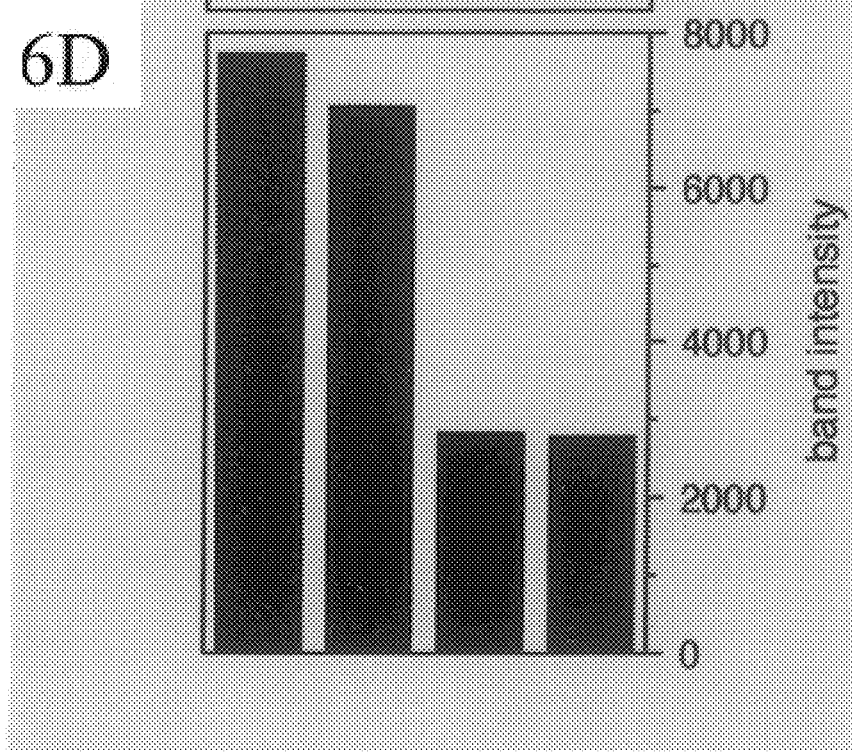

Electron microscopy was also performed on leaf tissue from transgenic tobacco expressing the 10 kD zein to check for the presence of any protein bodies. As seen in FIG. 5A and 5B, protein bodies very different from the 15 kD zein protein bodies (FIG. 5C) were seen in the leaves of the 10 kD zein plants. The protein bodies in the 10 kD zein plants appeared very osmophilic, the osmophilia being concentrated along the circumference of the bodies. In some cross sections, the osmophilia appeared to radiate in discrete spokes from a central hub (FIG. 5B). The protein bodies seen in the 15 kD zein plants did not exhibit this extreme osmophilia (FIG. 5C). In some of the leaf sections, the 10 kD zein protein bodies were found to be associated with the ER but in most cases because of the large size of the bodies the ER membranes appeared disjointed. Based on immunolocalization, the 10 kD zein was found to be evenly distributed in these unique protein bodies, suggesting that they result from assembly of the 10 kD zein (FIG. 5D).

Example 5

Simultaneous Accumulation of the 15 kD and 10 kD Zeins in Transformants Expressing both Genes Sexual crosses were made between tobacco transformants expressing either the 15 kD or 10 kD zeins in order to determine if these proteins interact with one another and affect protein accumulation in the plant cell. Seeds from these crosses were germinated on 200 μg/ml of kanamycin and seedlings expressing both genes were selected based on positive PCR using both 15 kD and 10 kD zein gene-specific primers. Protein extracts from the leaves of two independent plants expressing both genes and their respective parents were analyzed by immunoblotting using both 15 kD and 10 kD zein antibodies. The accumulation of the 15 kD zein protein appeared similar in both the parents and the 10 kD/15 kD zein crossed plants, while the accumulation of the 10 kD zein was many fold higher in the 10 kD/15 kD zein crossed plants compared to the corresponding 10 kD zein parent.

To determine the exact level of increase of the 10 kD zein due to co-expression with the 15 kD zein, equal amounts of the protein extracts from the leaves and seeds of one of the 10 kD zein plants, a 15 kD zein plant and the corresponding 10 kD/15 kD zein cross was analyzed by western analysis followed by quantitation of the immunoreactive bands using an Intelligent Quantifier (BioImage) (FIG. 6). This quantitative analysis shoed that the 15 kD zein levels in both the seeds and the leaves of the 10 kD/15 kD zein plants were essentially similar to those in the 15 kD zein parent plant (FIGS. 6C, 6D). However, the amount of 10 kD zein, was four- to five-fold higher in the leaves and seeds of the 10 kD/15 kD zein cross compared to the parent plant (FIGS. 6A, 6B). The level of the 15 kD and 10 kD zein in the cross or the parental lines cannot be compared directly with each other because of differences in the antigenicity of the two antibodies and the concentration of the antibodies used for developing the blots. These results also confirm previous studies indicating that the leaves accumulate more of the zein proteins than the seeds. Note that in case of the 10 kD zein protein (FIGS. 6A, 6B), the amount of protein loaded on the gel is 10 μg for the leaf samples and 50 μg for the seed samples.

Example 6

10 kD Zein Protein is Localized in the Same ER-derived Protein Bodies as the 15 kD Zein in Plants Co-expressing the 10 kD and 15 kD Zein Genes

Figure 7A:
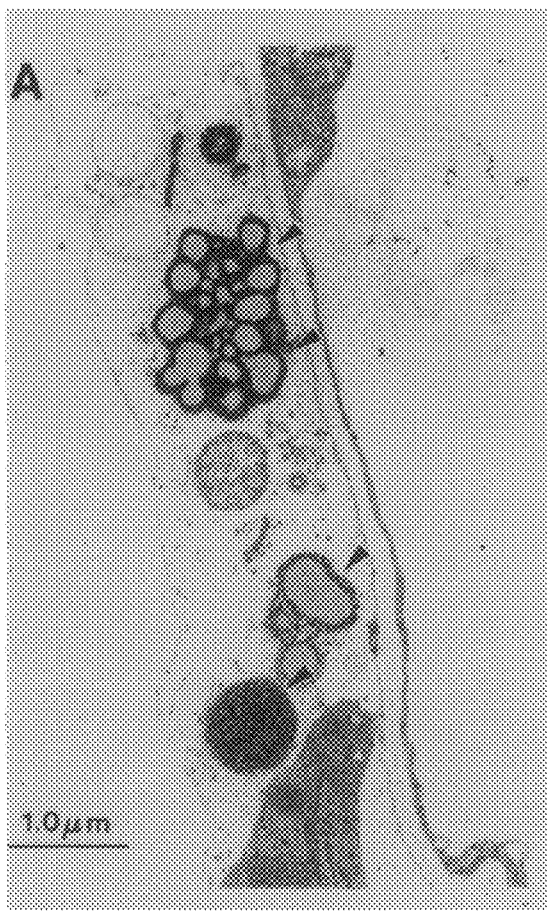
FIGS. 7A–7D. Subcellular localization of the 10 kD and 15 kD zeins in leaves of the 10 kD/15 kD zein plants.
Figure 7B:
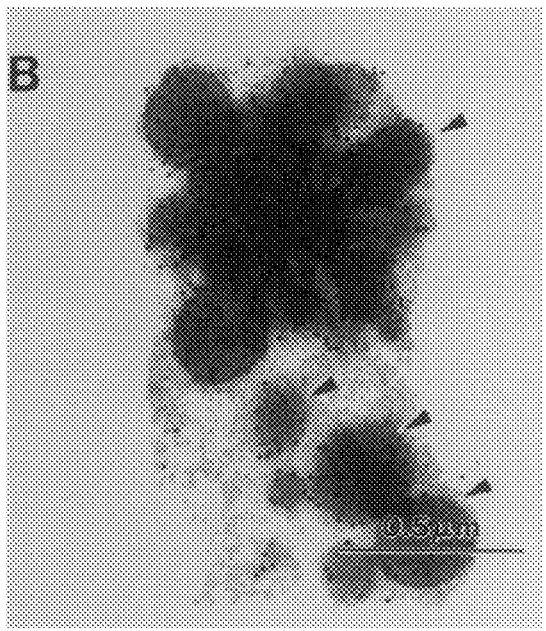
Figure 7C:
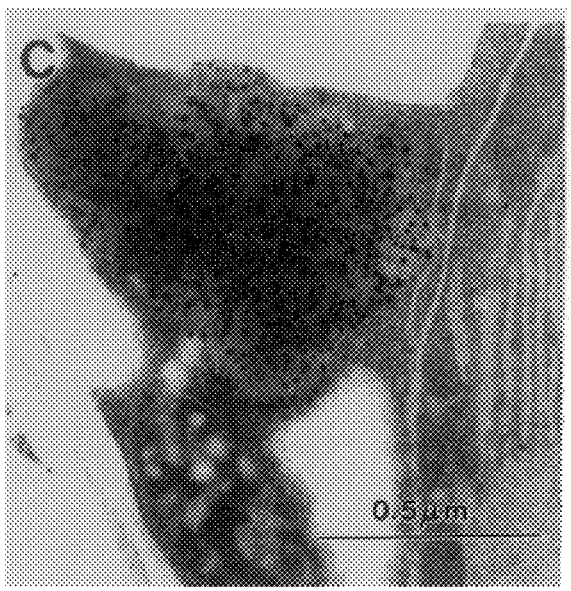
Figure 7D:
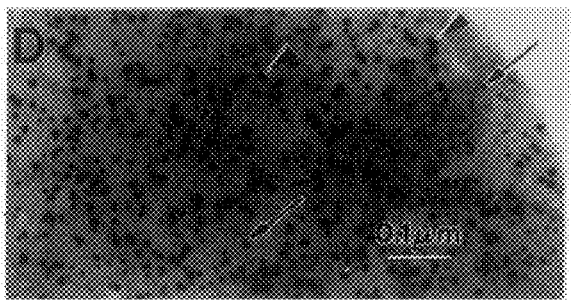

Increased accumulation of the 10 kD zein in the 10 kD/15 kD zein cross compared to the 10 kD zein plant alone is suggestive of some kind of interaction between the 10 kD and 15 kD zeins. Electron microscopy and immunocytochemistry of leaf tissue from a 10 kD/15 kD zein plant revealed only the ER-derived protein bodies typical for 15 kD zein (FIG. 7A). We did not observe any protein bodies similar to detected in the 10 kD zein plants. However, immunolocalization of 10 kD zein showed that the protein was exclusively confined in the 15 kD zein protein bodies (FIG. 7B). To determine whether the 10 kD zein and 15 kD zein were both located in the 15 kD zein protein bodies, we performed double-labeling immunocytochemistry on leaf and seed sections of the 10 kD/15 kD zein plant using monoclonal antibodies for the 10 kD zein and polyclonal antibodies for the 15 kD zein. Both the 10 kD zein (represented by the larger 10 nm gold particles) and 15 kD zein (represented by the smaller 5 nm gold particles) were immunolocalized in the same 15 kD zein protein bodies (FIG. 7C,D).Thus, the 15 kD and 10 kD zeins have been demonstrated to interact with one another and this interaction stabilizes the two proteins.

Example 7

Introduction of Multiple Copies of 15 kD and 10 kD Zein Genes into Alfalfa

Multiple copies of the 15 kD and 10 kD genes can be introduced in plants as a method of increasing the total leaf content of S-amino acid containing proteins. In addition to those constructs utilizing the 35S promoter, gene constructs driven by the SSU promoter and the mannopine synthase promoter can be used to avoid any potential problems of co-suppression. Isogenic populations carrying either the 10 kD, the 15 kD, or both the 10 kD and the 15 kD zein constructs can be sexually developed. Trends in zein dosage effects on expression "per se" in alfalfa, interactions between constructs, and the influence of each construct on plant development, forage quality and yield can be determined based on general comparisons of the average number of zein constructs expected within a population. Genetically defined genotypes from three populations carrying from one to four copies of either the 10 kD or 15 kD construct or one to two copies of both the 10 kD and 15 kD constructs can also be examined. The most direct approach to sexually increase zein copy number among regenerated somaclones would be to either self-pollinate individual regenerates or to intercross them. Intercrossing regenerants, however, is genetically equivalent to selfing in this case. To minimize the confounding effects of inbreeding depression a series of hybrid populations can be developed to examine the influence of zein constructs on forage yield and quality of alfalfa.

Example 8

Ruminant Digestion of Proteins

In ruminant animals, food is first acted upon by microorganisms inhabiting the first stomach (rumen) of the animal. The cellulose in plant material is digested by the inhabiting microorganisms since these animals do not produce cellulase on their own. These microorganisms, however, are also capable of breaking down plant proteins and utilizing the released amino acids for their own growth. These ruminant microbes are subsequently digested as they pass through rest of the digestive tract of the animal, thereby providing an important source of protein and other nutrients. However, a large part of these proteins are deminated in the nitrogen excreted in the urine. Not only does this reduce the nutritional quality of the feed material, it also results in excess nitrogenous environmental pollution. The problem is exacerbated when ruminant animals are given very high protein diets in an effort to maximize milk production. Amino acid supplements (e.g., methionine or lysine) are also subject to substantial degradation in the rumin and, thus, various rumin-protected amino acid supplements have been developed. Thus, it would be extremely desirable to feed intact proteins which are more resistant to microbial degradation. Therefore, it was important to determine if the zein proteins can be digested by the rumen bacteria and to determine if the zein proteins are digestible by the enzymes in the stomach of the ruminant animals.

Plant tissue was processed using mortar and pestle. Samples were placed into DACRON polyester bags (pore size 52 um). Approximately 0.3 g of each sample was kept for comparison purposes and the remaining amount was incubated inside the rumin of a cannulated Holstein cow for a period of 12 hours. Bags were then removed from the rumin, washed and dried in a 60 degree C. oven overnight. The 15 kD zein and 10 kD zein proteins were monitored immunologically (Western blotting) and by staining procedures. Ribulose biphosphate carboxylase which is highly degradable by ruminal bacteria (Nugent et al., 1983) was monitored and used as a internal control. Very low levels of zein degradation was observed, whereas the ribulose biphosphate carboxylase was completely degraded after the treatment. The levels of zeins in the treated and untreated samples was determined to be comparable. It was also determined that the zein protein is digested by stomach enzymes of ruminant animals.

Example 9

Induction of BiP in Transgenic Plants Expressing the Zein Genes

Figure 8:
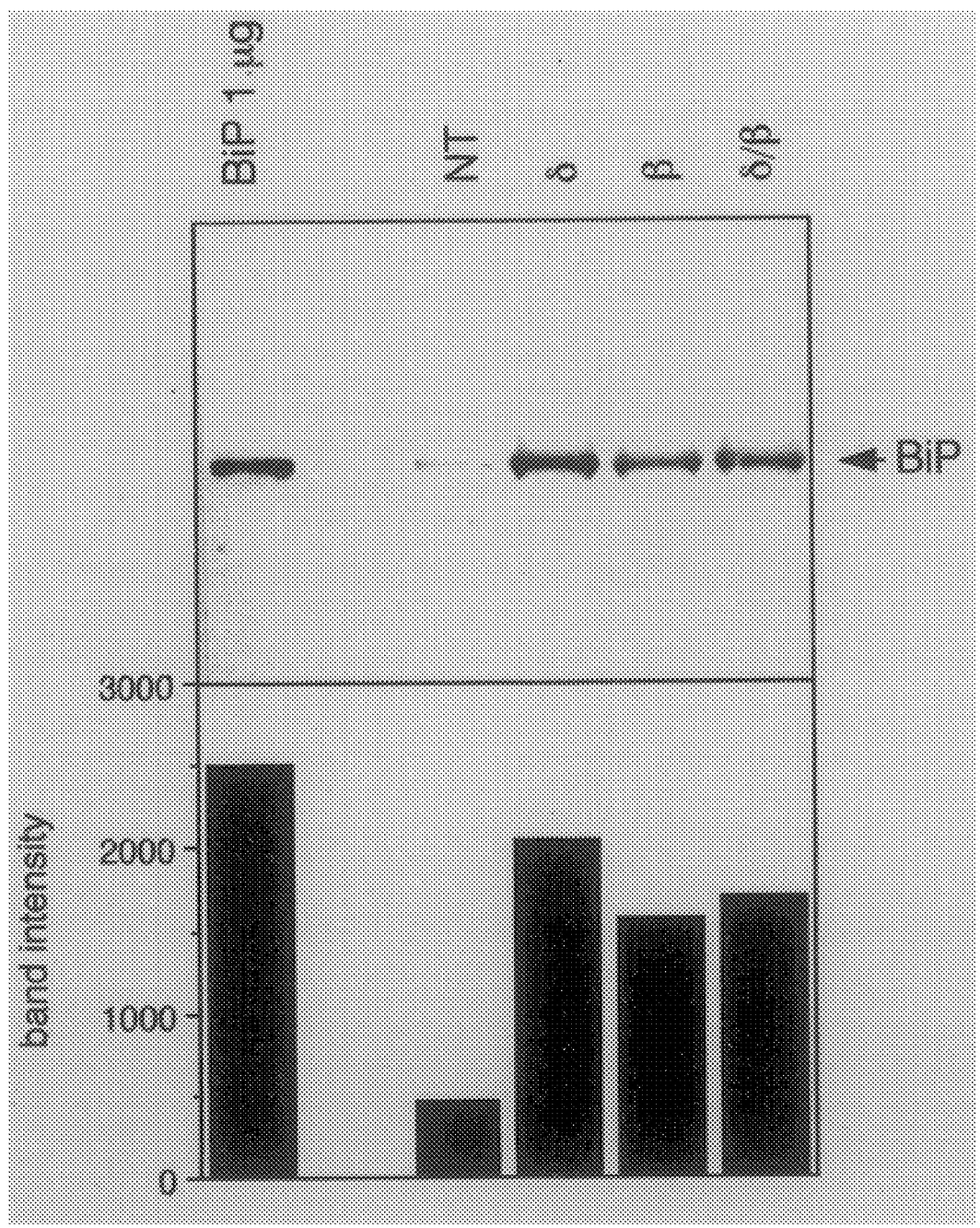
FIG. 8. Analysis of the accumulation pattern of BiP in the δ-, β-, and δ-/β-zein tobacco transformants.

Since BiP, an endogenous plant protein, has been implicated to have a role in prolamin protein body biogenesis (Li et al., 1993a; Zhang and Boston, 1991), it followed that BiP may have a role in the formation of zein protein bodies in transgenic tobacco plants. To test whether BiP is increased in plants making zein protein bodies, protein samples from leaves of δ-zein, β-zein and δ-/β-zein plants were subjected to quantitative western analysis using a corn BiP antibody (Zhang and Boston, 1992). The PBS soluble smaple (100 $\mu$g) from a control plant and three transgenic plants (δ-, β-, and δ-/β-zein plants) at the same developmental stage, all grown under the same conditions, along with 1 $\mu$g of purified BiP from corn, were subjected to SDS PAGE followed by western analysis (FIG. 8, top panel). The immunoreactive bands were then analyzed using the Intelligent Quantifier. The lower panel in FIG. 8 is the graphical representation of the relative intensity of the immunoreactive bands. All three transgenic plants showed a significantly higher level of BiP accumulation when compared to the control; the levels of BiP were more or less similar in the three transformants. Thus, the synthesis of the zein proteins in the transgenic plants induces the synthesis or stable accumulation of BiP.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Abe, S., W. You and E. Davis (1991) "Protein bodies in corn endosperm are enclosed by and enmeshed in F.-actin." *Protoplasma* 165:139–149.

Argos, P., K. Pederson, M. D. Marks and B. A. Larkins (1982) "A structural model for maize zein proteins" *J Biol. Chem.* 257:9984–9990.

Altenbach, S. B., C. C. Kua, L. C. Staraci, K. W. Pearson, C. Wainwright, A. Georgescu, and J. Townsend (1992) "Accumulation of a Brazil nut albumin in seeds of transgenic canola results in enhanced levels of seed protein methionine" *Pl. Mol. Biol.* 18:235–245.

Aycock, M. K., Jr., and C. P. Wilsie (1967) "Inbreeding Medicago sativa L. by sibmating: Cross-, sib- and self-fertility" *Crop Sci.* 7:281–284.

Bagga, S., Adams Hanke, J. D. Kemp, and C. Sengupta-Gopalan (1995) "Accumulation of 15 kD zein in novel protein bodies in transgenic tobacco" *Plant Physiol.* 107:13–23.

Barnes, D. K., B. P. Goplen, and J. E. Baylor (1988) "Highlights in the USA and Canada" In: A. A. Hanson, D. K. Barnes, and R. R. Hill, Jr. (ed.) Alfalfa and alfalfa improvement. Agron. Magr. 29. ASA, Madison, Wis.

Bednarek, S. Y. and N. V. Raikhel. (1991) "The barley lectin carboxy-terminal propeptide is a vacuolar sorting determinant in plants" *Plant Cell* 3:1195–1206.

Bingham, E. T. and T. J. McCoy (1979) "Cultivated alfalfa at the diploid level: Origin, reproductive stability, and yield or seed and forage" *Crop Sci.* 19:97–100.

Bingham, E. T. (1983a) "Maximizing hybrid vigor in autotetraploid alfalfa. P. 130–143. In Better Crops for Food. CIBA Found Symp. 97. Pitman Books, London.

Bingham, E. T. (1983b) "Molecular genetic engineering vs. Plant breeding" *Plant Mol. Biol.* 2:221–228.

Boston, R. S., E. B. P. Fontes, B. B. Shank and R. L. Wrobel (1991) "Increased expression of the maize immunoglobulin binding protein homology b-70 in three zein regulatory mutants" *Plant Cell* 3:497–505.

Ceriotti, A., E. Pedrazzini, M. S. Fabbrini, M. Zoppe, R. Bollini and A. Vitale (1991) "Expression of the wild type and mutated vacuolar storage protein phaseolin in *xenopus oocytes* reveals relationships between assembly and intracellular transport. *Eur. J Biochem.* 202:959–968.

Chrispeels, M. J. (1991) "Sorting of protein in the secretory system" Annu. Rev. Plant Physiol. *Plant Mol. Biol.* 42:21–53.

Chrispeels, M. J. and N. V. Raikhel (1992) "Short peptide domains target proteins to plant vacuoles" *Cell* 68:613–616.

De Barros, E. G. and B. A. Larkins (1990) "Purification and characterization of zein degrading proteinases from germinating maize endosperm" *Plant Physiol.* 94:297–303.

DeClercq, A., M. Vandewlele, R. De Rycke, J. Van Damme, M. Van aMontagu, E. Krebbers, J. Vandekerckjove (1990) "Expression and processing of an Arabidopsis 2S albumin in transgenic tobacco" *Plant Physiol.* 94:970–979.

Dunbier, M. W., and E. T. Bingham (1975) "Maximum heterozygosity in alfalfa: Results using haploid-derived autotetraploids" *Crop Sci.* 15:527–531.

Edwards, G. A., A. Hepher, S. P. Clerk and D. Boulter (1991) "Pea lectin is correctly processed, stable and active in leaves of transgenic potato plants" *Plant Mol. Biol.* 17:89–100.

Esen, A. and D. A. Stetter (1992) "Immunochemical location of γ-zein in the protein bodies of maize endosperm" *Am. J Bot.* 79:243–248.

Finnegan, J. and D. McElroy (1994) "Transgene Inactivation: Plants fight back!" *Biotechnology* 12:883–888.

Flavell, R. B. (1994) "Inactivation of gene expression in plants as a consequence of specific sequence duplication. *Proc. Natl. Acad. Sci. USA* 91:3490–3496.

Gallais, A. (1984) "An analysis of heterosis vs. Inbreeding effects with an autotetraploid cross-fertilized plant: Medicago stiva L" *Genetics* 106:123–137.

Giannazza, E., V. Viglienghi, P. B. Righetti, F. Salamini, and C. Soave (1977) "Amino acid composition of zein molecular components" *Phytochemistry* 16:315–317.

Galili, G. (1995) "Regulation of lysine and threonine synthesis" *The Plant Cell* 7:899–906.

Goldsbrough, P., B., S. B. Gelvin and B. A. Larkins (1986) "Expression of maize zein genes in transformed sunflower cells" *Mol. Gen. Genet.* 202:374–381.

Groose, R. W., W. P. Kojis, and E. T. Bingham (1988) "Combining ability differences between isogenic diploid and tetraploid alfalfa" *Crop Sci.* 28:7–10.

Groose, R. W., L. E. Talbert, W. P. Kojis, and E. T. Bingham (1989) "Progressive heterosis in autotetraploid alfalfa: studies using two types of inbreds" *Crop Sci.* 29:1173–1177.

Guerche, P., E. R. P. De Almeida, M. A. Schwarztein, E. S. Gander, E. Krebbers, and G. Pelletier (1990) "Expression of the 2S albumin from *Bertholletia exceisa* in *Brassica napus*" *Mol. Gen. Genet.* 221:305–314.

Hanson, A. A., D. K. Barnes, and R. R. Hill (1988) "Alfalfa and Alfalfa improvements" Agronomy Monographs 29, ASA, CSSA and SSA, Madison Wis. USA.

Hilder, V. A., A. M. R., Gatehouse, S. E. Sheerman, R. F. Barker and D. Boulter (1987) "A novel mechanism of insect resistance engineered into tobacco" *Nature* 300:160–163.

Hoffman, L. M., D. D. Donaldson, R. Bookland, K. Rashka, and E. M. Herman (1987) "Synthesis and protein body deposition of maize 15 kD zein in transgenic tobacco seeds" *EMBO. J.* 6:3213–3221.

Hoffman, L. M., Donaldson, and E. M. Herman (1988) "A modified storage protein is synthesized, processed and degraded in the seeds of transgenic plants" *Plant Mol. Biol.* 11:717–729.

Jorgensen, R. A. (1995) "Cosuppression, flower color patterns, and metastable gene expression states" *Science* 268:686–691.

Kaldy, M. S., M. R. Hanna, S. Smoliak (1979) "Aminoacid composition of santoin forage" *Grass and Forage Sci.* 34:145–148.

Karchi, H., O. Shaul and G. Galili (1993) "Seed-specific expression of a bacterial disensitized aspartate kinase increases the production of seed threonine and methionine in transgenic tobacco" *The Plant J.* 3:721–727.

Kempthorne, O. (1969) "An introduction to genetic statistics" Iowa State University Press, Ames.

Kirhara, J. A., J. P. Hunsperger, W. C. Mahoney, and J. W. Messing (1988) "Differential expression of a gene for a methionine-rich storage protein in maize" *Mol. Gen. Genet.* 211:477–484.

Langridge, P. and G. Felix (1983) "A zein gene of maize is transcribed from two widely separated promoter regions" *Cell* 34:1015–1022.

Larkins, B. A., C. R. Lending, J. C. Wallace, G. Galili, E. E. Kawata, K. B. Geetha, A. L. Kirz, D. M. Martin, and C. E. Bracker (1989) "Zein gene expression during maize endosperm development" In: Goldbert R. B. (Ed) *The molecular basis of plant development*, Alan R. Liss, NY pp. 109–120.

Larkins, B. A. and W. J. Hurkman (1978) "Synthesis and deposition of zein in protein bodies of maize endosperm" *Plant Physiol.* 62:256–263.

Lee, K. H., R. A. Jones, A. Dalby, and C. Y. Tsai (1976) "Genetic regulation of storage protein content in maize endosperm" *Biochemical Genetics* 14:641–650.

Lending, C. R. and B. A. Larkins (1989) "Changes in the zein composition of protein bodies during maize endosperm development" *Plant Cell* 1:1011–1023.

Levanony, H., R. Rubin and Galili G. Altschuler (1992) "Evidence for a novel rout of wheat storage proteins to vacuoles" *J. Cell Biol.* 119:1117–1128.

Li, X., Franceshi, V. R. and T. W. Okita (1993a) "Segregation of storage protein mRNAs on the rough endoplasmic reticulum membranes of rice endosperm cells" *Cell* 72:869–879.

Li, X., Wu, Y., D -Z Zhang, J. W. Gillikin, R. S. Boston, V. R. Franceschi and T. W. Okita (1993b) "Rice prolamine protein body biogenesis: a BiP-mediated process" *Science* 262: 1054–1056.

Matsuoka, K., K. Nakamura (1991) "Propeptide of a precursor to a plant vacuolar protein required for vacuolar targeting" *PNAS USA* 88:834–838.

Maliga, P. (1978) "Resistant mutant and thier use in genetic manipulation" In: *Frontiers of plant tissue culture* (Ed: Thorpe TA) pp 381–392.

Masumura, T., T. Hibino, K. Kidza, N. Mitsukawa, K. Tanaka and S. Fujii (1990) "Cloning and characterization of a cDNA encoding a rice 13kD prolamin" *Mol. Gen. Genet* 221:1–7.

Meyer, P. and I. Heidman (1994) "Epigenetic variants of a transgenic petunia line shows hypermethylation in transgene DNA: an inidcation for specific recognition of foreign DNA in transgenic plants" *Mol. Gen. Genet.* 243:390–399.

Michaud, R., W. F. Lehman, and M. D. Rumbaugh (1988) "World distribution and historical development" In A. A. Hanson, D. K. J. Barnes, and R. R. Hill, Jr. (Ed) Alfalfa and alfalfa improvement. Agron. Mongr. 29, ASA, Madison, Wis.

Minson, D. J. (1990) Protein. In: Forage in Ruminant Nutrition, Academic Press Inc., New York).

Misra, P. S., R. Jumbunathan, E. T. Mertz, D. V. Glover, H. M. Barbosa, K. S. McWhirter (1972) "Endosperm protein synthesis in maize mutants with increased lysine content" *Science* 176:1425–1426.

Nugent, J. H. A., W. T. Jones, D. J. Jones and J. L. Mangan (1983) "Rates of proteolysis in the rumen of the soluble proteins casein, Fraction I (18S) leaf protein bovine serum and bovine submaxlllary mucoprotein" *Br. J Nutr.* 50:357–368.

Ohtani, T., J. C. Wallace, G. A. Thompson, G. Galili, and B. A. Larkins (1990) "Normal and lysine containing zeins are unstable in transgenic tobacco seeds" *Plant Mol. Biol.* 15:117–128.

Pelham, H. R. B. (1990) "The retention signal for soluble proteins of the endoplasmic reticulum" *Trends Biochem Sci.* 15:483–485.

Phillips, R. L., B. A. McClure (1985) "Elerated protein bound methionine in seeds of maize line resistant to lysine plus threonine cereal chem. 62:213–218.

We claim:

1. A method for increasing the stability and storage of a second heterologous protein in a plant, comprising transforming plant tissue with a polynucleotide molecule that encodes a first heterologous storage protein selected from the group consisting of 15 kD zein and 0 kD zein; and obtaining a transgenic plant from said plant tissue, said first heterologous storage protein being expressed and accumulated as a protein body in a vegetative tissue of said plant, said plant also comprising a second heterologous protein selected from the group consisting of 15 kD zein and 10 kD zein, wherein said plant co-expresses both the 15 kD zein and 10kD zein proteins and the stability of said second heterologous protein is increased.

2. The method, according to claim 1, wherein said storage protein is rumin stable.

3. A transgenic plant or transgenic plant tissue comprising at least one 15 kD zein protein that is co-expressed with at least one 10 kD zein storage protein and accumulated as a protein body in a vegetative tissue of said plant or plant tissue.

4. A method for increasing forage quality of members of a plant species, comprising transforming plant tissue and obtaining a transgenic plant therefrom such that at least one 15 kD zein protein is co-expressed with at least one 10 kD zein storage protein and accumulates as a protein body in vegetative tissue of said plant.

5. The method of claim 1 further comprising the steps of obtaining descendants of said plant and growing said descendants under conditions whereby said 15 kD zein and said 10 kD zein are co-expressed.

6. The methods of claim 4 further comprising the steps of obtaining descendants of said plant and growing said descendants under conditions whereby said 15 kD zein and said 10 kD zein are co-expressed.

* * * * *

UNITED STATES PATENT AND TRADEMARK OFFICE
CERTIFICATE OF CORRECTION

PATENT NO. : 5,990,384

DATED : November 23, 1999

INVENTOR(S) : Suman Bagga, Champa Sengupta-Gopalan, John D. Kemp

It is certified that error appears in the above-identified patent and that said Letters Patent is hereby corrected as shown below:

Column 3, line 16: "the a zein" should read --the α zein--.

Column 18, line 16: "and 0 kD zein;" should read --and 10 kD zein--.

Signed and Sealed this

Twenty-sixth Day of September, 2000

Attest:

Q. TODD DICKINSON

*Attesting Officer*      *Director of Patents and Trademarks*